United States Patent [19]

Karbowniczak

[11] Patent Number: 5,050,729
[45] Date of Patent: Sep. 24, 1991

[54] TOOTH STORAGE CONTAINER

[76] Inventor: Edith M. Karbowniczak, P.O. Box 0493, E. Syracuse, N.Y. 13057

[21] Appl. No.: 564,117

[22] Filed: Aug. 8, 1990

[51] Int. Cl.$^5$ .................... A61C 19/10; B65D 27/04
[52] U.S. Cl. ............................ 206/83; 206/45.31; 206/462; 206/813; 229/71; 383/40; 383/106
[58] Field of Search .............. 206/83, 45.31, 45.34, 206/461, 462, 463, 813; 150/143, 145, 152; 383/40, 86, 106; 229/71

[56] References Cited

U.S. PATENT DOCUMENTS

| | | | |
|---|---|---|---|
| 597,325 | 1/1898 | Prickett | 150/152 |
| 897,777 | 9/1908 | Pflueger | 229/71 |
| 1,185,723 | 6/1916 | Scheuer | 150/143 |
| 1,687,436 | 10/1928 | Fort | 229/71 |
| 2,318,618 | 5/1943 | Myerson et al. | 206/83 |
| 2,363,997 | 11/1944 | Rothman | 206/83 |
| 2,685,550 | 8/1954 | Corey | 150/143 X |
| 2,805,183 | 9/1957 | Higgins | 206/813 X |
| 2,925,675 | 2/1960 | Lumpkin | 206/813 X |
| 3,509,991 | 5/1970 | Hurst | 206/813 X |
| 3,789,546 | 2/1974 | Morrison | 5/485 X |
| 4,091,481 | 5/1978 | Redman | 5/434 |
| 4,768,245 | 9/1988 | Dutton | 5/434 |
| 4,783,120 | 11/1988 | Kiechlin | 297/230 |

*Primary Examiner*—Bryon P. Gehman
*Attorney, Agent, or Firm*—Leon Gilden

[57] ABSTRACT

A container organization wherein a front and rear wall define an envelope body with the forward wall including a V-shaped recess with a flap selectively overlying the forward wall including cooperative snap fasteners mounted to the forward wall and bottom surface of the flap. A flexible adhesive strip with a peel away layer is mounted to the rear wall to permit subsequent securement of the organization within a book and the like. A through extending transparent window member is mounted through the forward wall with a peel away opaque surface overlying the wall to permit storage and viewing of a tooth therethrough with the peel away layer including a further peel away strip to be secured within the envelope to overlie a rear wall of the window member and sealingly secure the tooth therewithin.

4 Claims, 4 Drawing Sheets

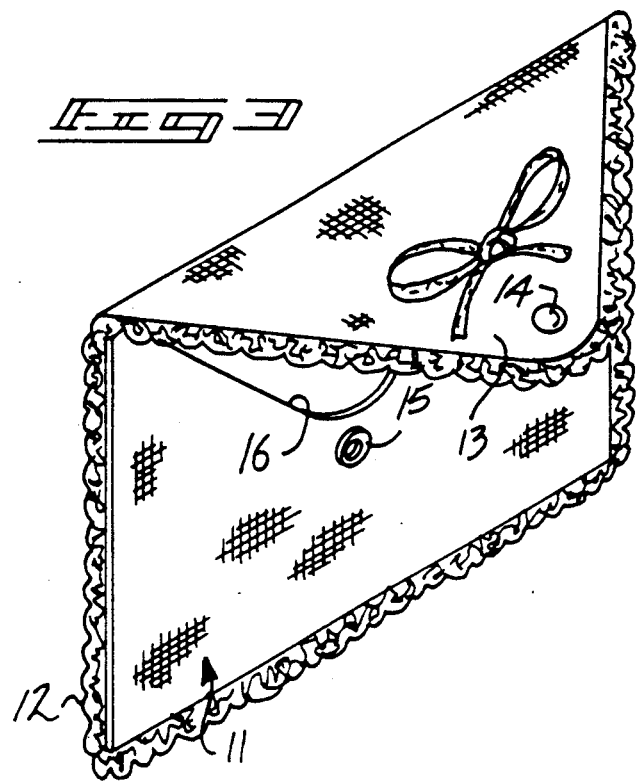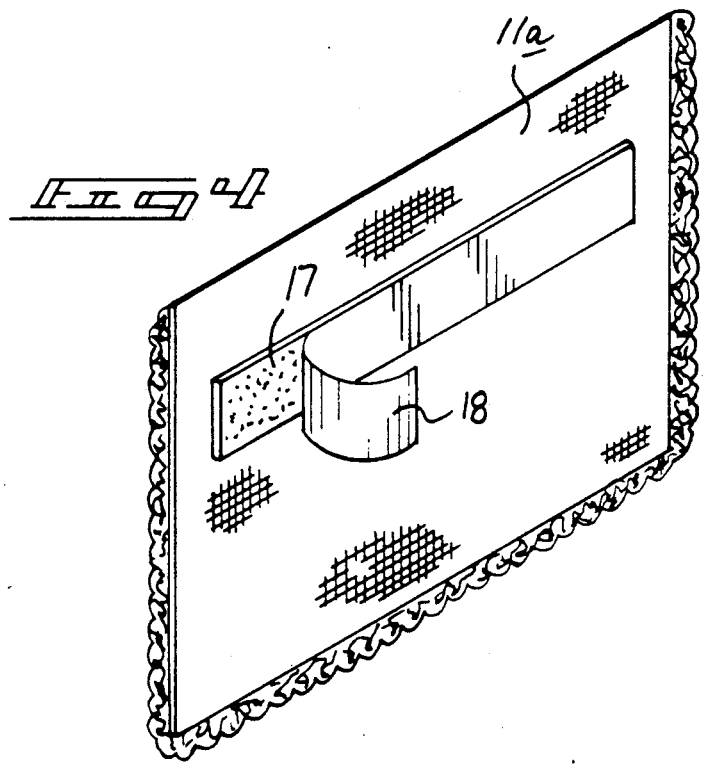

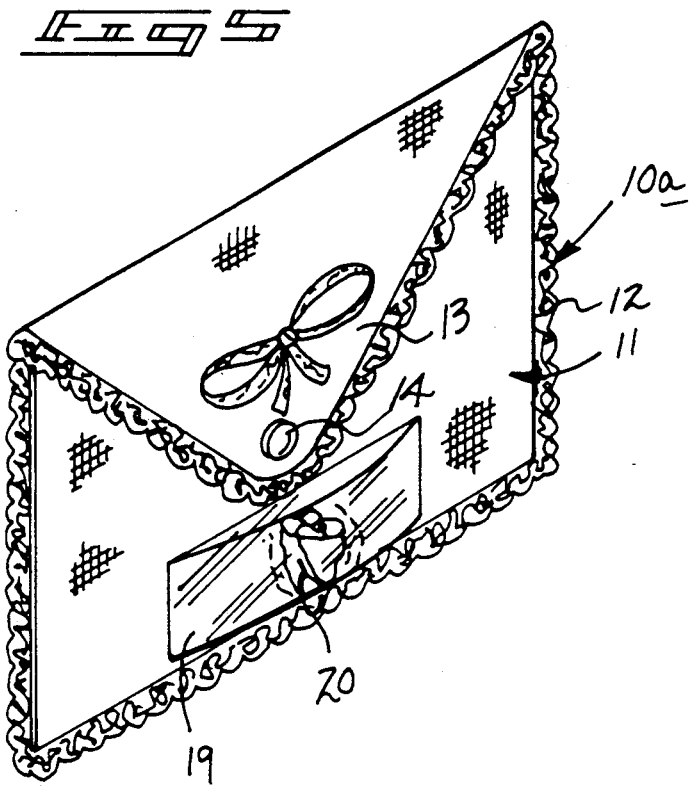
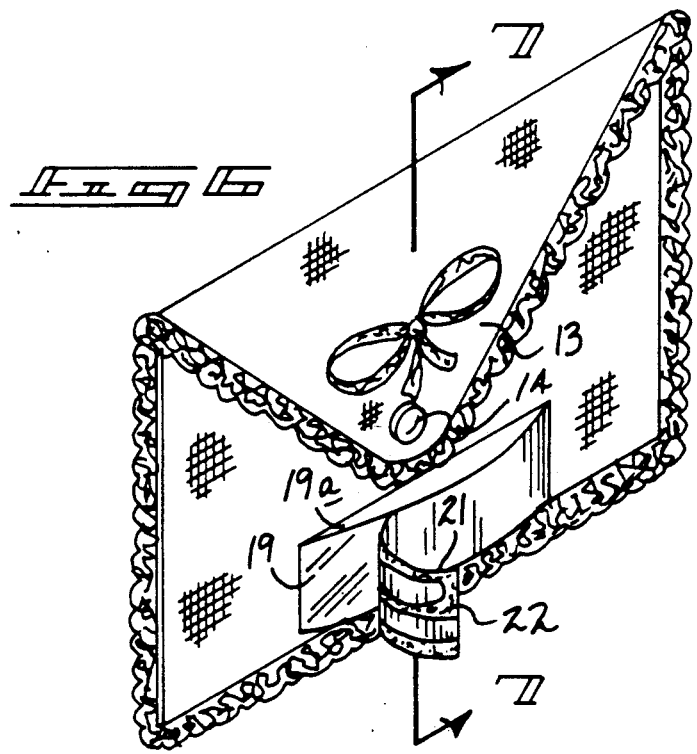

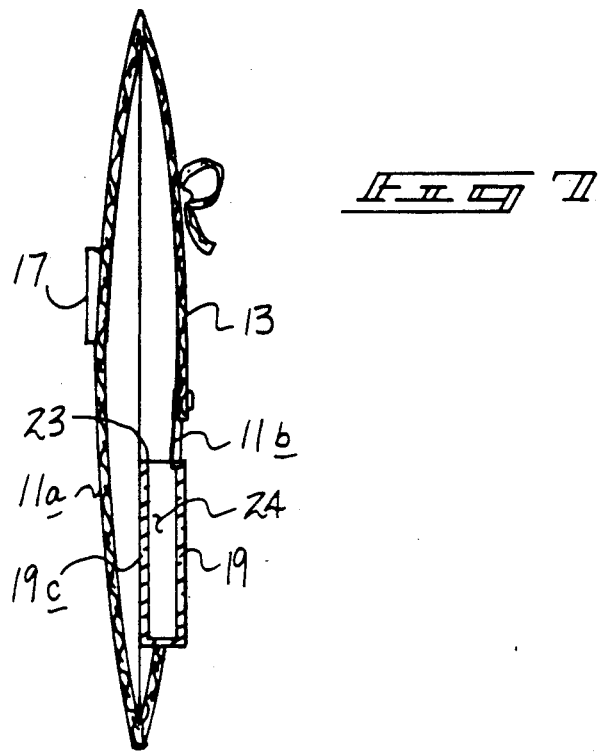
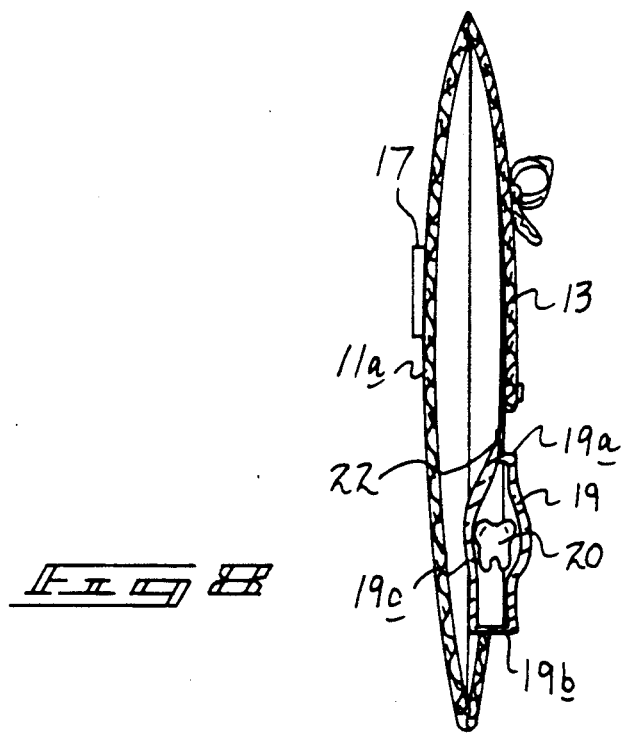

TOOTH STORAGE CONTAINER

BACKGROUND OF THE INVENTION

1. Field of the Invention

The field of the invention relates to tooth storage apparatus, and more particularly pertains to a new and improved tooth storage container wherein the same permits reception of a child's tooth therewithin for subsequent exchange of the tooth for money and the like to be inserted within the envelope for entertainment and amusement of a child.

2. Description of the Prior Art

Various tooth storage containers have been utilized in the prior art. Heretofore however the prior art organization has failed to provide a flexible and adaptable organization permitting storage and viewing of the tooth structure as well as permitting transfer of the tooth in exchange for money for the amusement and entertainment of a child. Prior art structure may be found in U.S. Pat. No. 4,091,481 to REDMAN wherein a tooth pillow of a generally tooth like structure includes a pocket mounted to a forward wall of the pillow.

U.S. Pat. No. 4,768,245 to DUTTON sets forth a pillow organization with a pocket mounted therewithin for securement of book and the like for a child.

U.S. Pat. No. 3,789,546 to MORRISON sets forth a pillow with a puppet member receivable within a pocket thereof to permit a child to position a hand inside the doll to manipulate the same in a manner as a puppet.

U.S. Pat. No. 4,783,120 to KIECHLIN sets forth a seat cushion employing a attachable pocket for carrying incidental items and in a modified form including a back rest.

As such, it may be appreciated that there continues to be a need for a new and improved tooth storage container apparatus as set forth by the instant invention which addresses both the problems of ease of use as well as effectiveness in the entertainment and amusement of a child as well as for the permanent storage of a tooth therewithin and in this respect, the present invention substantially fulfills this need.

SUMMARY OF THE INVENTION

In view of the foregoing disadvantages inherent in the known types of tooth storage containers present in the prior art, the present invention provides a new and improved tooth storage container wherein the same provides for an envelope for the mounting and storage of a tooth as well as the transfer of and exchange of money for the tooth for the entertainment of a child. As such, the general purpose of the present invention, which will be described subsequently in greater detail, is to provide a new and improved tooth storage container which has all the advantages of the prior art tooth storage container and none of the disadvantages.

To attain this, the tooth storage container of the instant invention includes a container organization wherein a front and rear wall define an envelope body with the forward wall including a V-shaped recess with a flap selectively overlying the forward wall including cooperative snap fasteners mounted to the forward wall and bottom surface of the flap. A flexible adhesive strip with a peel away layer is mounted to the rear wall to permit subsequent securement of the organization within a book and the like. A through extending transparent window member is mounted through the forward wall with a peel away opaque surface overlying the wall to permit storage and viewing of a tooth therethrough with the peel away layer including a further peel away strip to be secured within the envelope to overlie a rear wall of the window member and sealingly secure the tooth therewithin.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved tooth storage container which has all the advantages of the prior art tooth storage container and none of the disadvantages.

It is another object of the present invention to provide a new and improved tooth storage container which may be easily and efficiently manufactured and marketed.

It is a further object of the present invention to provide a new and improved tooth storage container which is of a durable and reliable construction.

An even further object of the present invention is to provide a new and improved tooth storage container which is susceptible of a low cost of manufacture with regard to both materials and labor, and which accordingly is then susceptible of low prices of sale to the consuming public, thereby making such tooth storage containers economically available to the buying public.

Still yet another object of the present invention is to provide a new and improved tooth storage container which provides in the apparatuses and methods of the prior art some of the advantages thereof, while simultaneously overcoming some of the disadvantages normally associated therewith.

Still another object of the present invention is to provide a new and improved tooth storage container which may be compactly stored when not being utilized.

Yet another object of the present invention is to provide a new and improved tooth storage container wherein the same permits a convenient storage and containment of a tooth and money in exchange therefore as well as a permanent mounting and storage of the organization subsequent to its use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an isometric illustration of the instant invention.

FIG. 4 is an isometric illustration of a rear wall of the instant invention.

FIG. 5 is an isometric illustration of the instant invention including a transparent window and storage pocket mounted to the forward wall.

FIG. 6 is an isometric illustration of the instant invention including a peal away strip removable from a forward surface of the transparent window.

FIG. 7 is an orthographic view taken along the lines 7—7 of FIG. 6 in the direction indicated by the arrows.

FIG. 8 is an orthographic cross-sectional view of the invention with a sealing strip mounted overlying a free edge portion of the window to sealingly secure its contents therewithin.

DESCRIPTION OF THE PREFERRED EMBODIMENT

Figure 1:
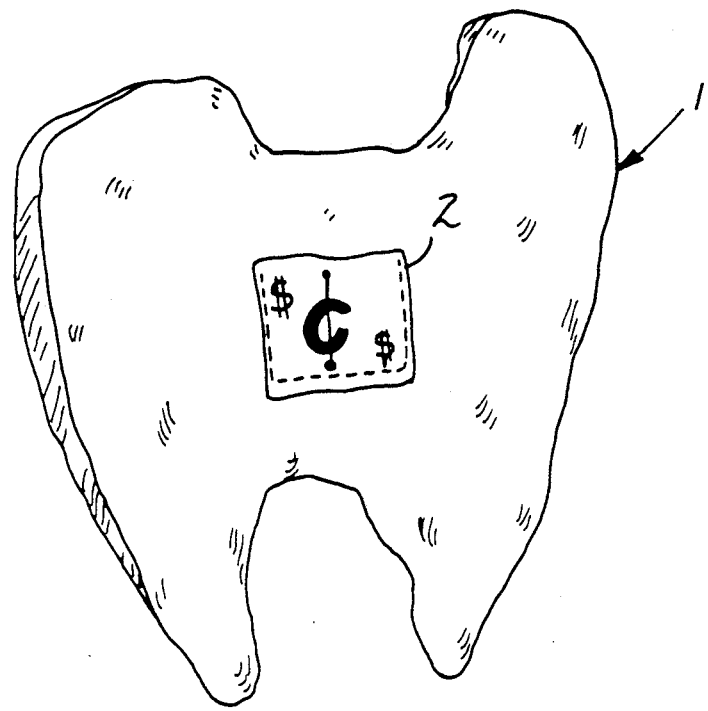
FIG. 1 is an isometric illustration of a prior art tooth storage container.
Figure 2:
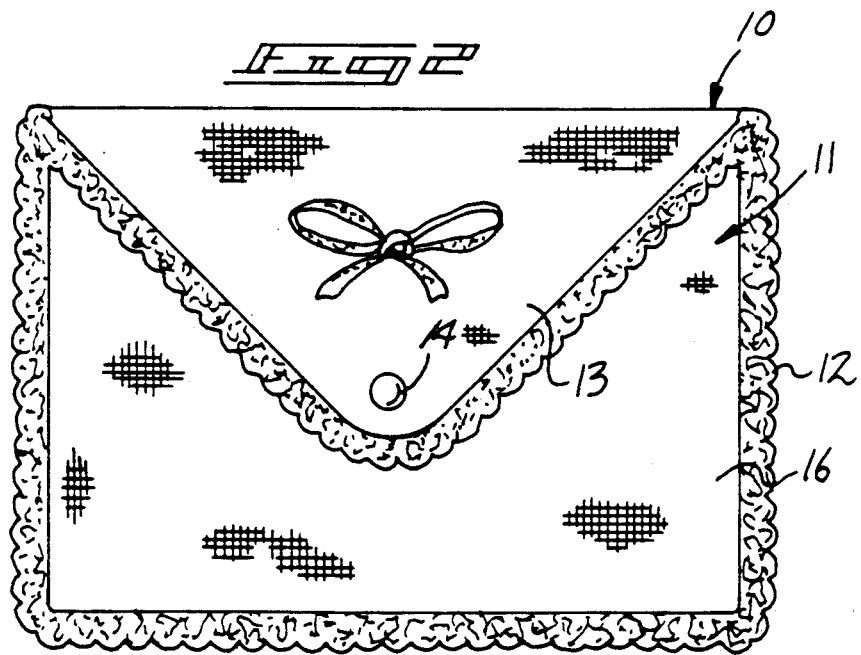
FIG. 2 is an orthographic frontal view taken in elevation of the instant invention.

With reference now to the drawings, and in particular to FIGS. 1 to 8 thereof, a new and improved tooth storage container embodying the principles and concepts of the present invention and generally designated by the reference numerals 10 and 10a will be described.

FIG. 1 is an isometric illustration of a prior art tooth storage organization formed as a pillow in a configuration as a tooth with a pocket member 2 for the receiving of a tooth and monetary exchange therefor within the pocket.

More specifically, the tooth storage container 10 of the instant invention essentially comprises an envelope body 11 that includes a rear surface wall 11a and a forward surface wall 11b. The forward wall 11b includes a cover flap 13 that overlies a V-shaped recess 16 that is formed downwardly from an upper edge of the forward wall and is covered by the triangular cover flap 13. The cover flap 13 includes a first snap fastener 14 mounted adjacent a lower apex of the cover flap 13 cooperative with a second snap fastener member 15 that is mounted within the forward wall 11b adjacent a lower apex of the V-shaped recess 16 in a manner as illustrated in FIG. 3. A lace type fringe perimeter 12 is mounted about the edge of the envelope body 11 to include the cover flap 13.

An adhesive strip 17 is mounted longitudinally of the rear wall 11a and includes a first peel away flexible layer 18 that is removable to permit subsequent mounting of the envelope body within a memorabilia type container or a family reference organization such as a book and the like (not shown).

Reference to FIGS. 5 through 8 illustrates the use of a convex transparent window pouch mounted through the forward wall 11b and extending through the forward wall 11b to the interior cavity defined by the envelope body 11 in a manner as illustrated in FIGS. 7 and 8. The transparent window 19 includes a window top wall 19a and a window bottom wall 19b that extend through the forward wall 11b of the envelope body in a orthogonal relationship to permit extension of the window for enhanced viewing of its contents such as a tooth element 20 in a manner as illustrated in FIG. 8. An opaque second peal away layer 21 is coextensively mounted overlying the window 19 and the peel away layer itself includes a third peel away layer 22 mounted to a rear surface of the second peel away layer 21 whereupon a mounting of a tooth element 20 within the cavity defined by the window 19, the third peel away layer 22 is positioned to secure the top rear wall edge 23 of the rear wall 19c to seal the tooth element 20 within the pocket 24 of the window 19.

It is understood that in use, a child may position a tooth member within the envelope 19 for subsequent exchange in a conventional and historical manner for the entertainment and amusement of the child. Subsequently, to permit the storage and convenient viewing of the tooth, the tooth element 20 is positioned within the pocket 24 and sealed therewithin by the third peal away layer 22 in a manner as noted above and may thereby after be positioned within a book or upon a storage surface upon removal of the first peal away layer 18 to expose the adhesive strip 17.

As to the manner of usage and operation of the instant invention, the same should be apparent from the above disclosure and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A tooth storage container comprising in combination, an envelope body, the envelope body including a forward wall positioned adjacent to a rear wall with the forward wall and rear wall defining an envelope body cavity therebetween, a V-shaped recess is directed downwardly and medially of an upper edge of the forward wall and a cover flap mounted to the rear wall is arranged to complementarily overlie the V-shaped recess,
and
the cover flap defined by a triangular configuration, the cover flap including a first snap fastener member mounted adjacent a medially oriented apex of the cover flap to cooperate with a second snap fastener member with the second snap fastener member mounted through the forward wall adjacent a lower apex of the V-shaped recess,
and
wherein an adhesive strip is mounted longitudinally of the rear wall and includes a first peel away flexible layer overlying the adhesive strip to permit selective exposure of the adhesive strip for mounting of the envelope body,
and
wherein the forward wall includes a convex transparent window mounted through the forward wall with the window including a window top wall and a window bottom wall with the window top wall and window bottom wall each arranged orthogonally relative to the forward wall of the envelope body to protrude the window beyond the forward wall, and the window defining a pocket with a rear wall directed through the forward wall and interiorly of the envelope body coextensively with the window to define a pocket.

2. A container as set forth in claim 1 wherein the window includes a second peel away layer coextensively overlying the window.

3. A container as set forth in claim 2 including third peel away layer means adhesively and rearwardly mounted to a rear surface of the second peel away layer the second peel away layer and the window for removal of the third peel away layer from the second peel away layer.

4. A container as set forth in claim 3 wherein the rear wall of the pocket includes a top rear wall edge extending interiorly of the envelope body to permit receipt of a tooth element within the pocket.

* * * * *